United States Patent
Sherry et al.

(10) Patent No.: US 6,939,134 B2
(45) Date of Patent: Sep. 6, 2005

(54) CHEEK, LIP AND TONGUE SHIELD

(75) Inventors: Ronald Sherry, Lehighton, PA (US); Jude Gaydos, Orwigsburg, PA (US)

(73) Assignee: EZ Retractor, Inc., Orwigsburg, PA (US)

( * ) Notice: Subject to any disclaimer, the term of this patent is extended or adjusted under 35 U.S.C. 154(b) by 84 days.

(21) Appl. No.: 10/604,017

(22) Filed: Jun. 21, 2003

(65) Prior Publication Data

US 2004/0259055 A1 Dec. 23, 2004

(51) Int. Cl.$^7$ ................................................ A61C 5/00
(52) U.S. Cl. ............................................. 433/140
(58) Field of Search ............................... 433/136, 140; 600/237, 238, 239, 240, 241, 242

(56) References Cited

U.S. PATENT DOCUMENTS

| | | | |
|---|---|---|---|
| 730,184 A | | 6/1903 | Witter |
| 965,079 A | * | 7/1910 | Caswell ........................ 433/30 |
| 990,277 A | * | 4/1911 | Lauderdale ................... 433/89 |
| 1,474,497 A | | 11/1923 | Stolper |
| 1,498,267 A | * | 6/1924 | Hachman ...................... 433/89 |
| 2,125,980 A | | 8/1938 | Basil |
| 2,831,480 A | | 4/1958 | Milano |
| 4,112,934 A | | 9/1978 | Rizk |
| 4,259,068 A | | 3/1981 | Stephens |
| 4,971,557 A | | 11/1990 | Martin |
| 5,490,780 A | * | 2/1996 | Riewenherm ................. 433/93 |
| 5,730,597 A | | 3/1998 | Luttrell |
| 5,813,857 A | * | 9/1998 | Hertz ........................... 433/93 |
| 5,873,718 A | | 2/1999 | Sullivan |
| 5,890,899 A | | 4/1999 | Sclafani |
| 6,102,701 A | | 8/2000 | Engeron |
| 6,213,772 B1 | | 4/2001 | Costello |
| 6,267,591 B1 | | 7/2001 | Barstow |

* cited by examiner

*Primary Examiner*—Cary E. O'Connor
(74) *Attorney, Agent, or Firm*—Mitchell A. Smolow

(57) ABSTRACT

The present invention discloses a cheek, lip and tongue shield comprising a handle having a first and second end, the first end for gripping; a first shield having an anterior end, a posterior end, and an inferior border, the anterior end transitioning from the handle second end; a non-hinging transverse member having a first and second end, the first end transitioning from the first shield posterior end; and a second shield having an anterior end, a posterior end, and an inferior border, the posterior end transitioning from the transverse member second end. The transverse member inferior border does not extend as far inferiorly as the first and second shield inferior borders, the first shield passively isolates the cheek and lip from the operative site, and the second shield passively isolates the tongue from an operative site.

27 Claims, 2 Drawing Sheets

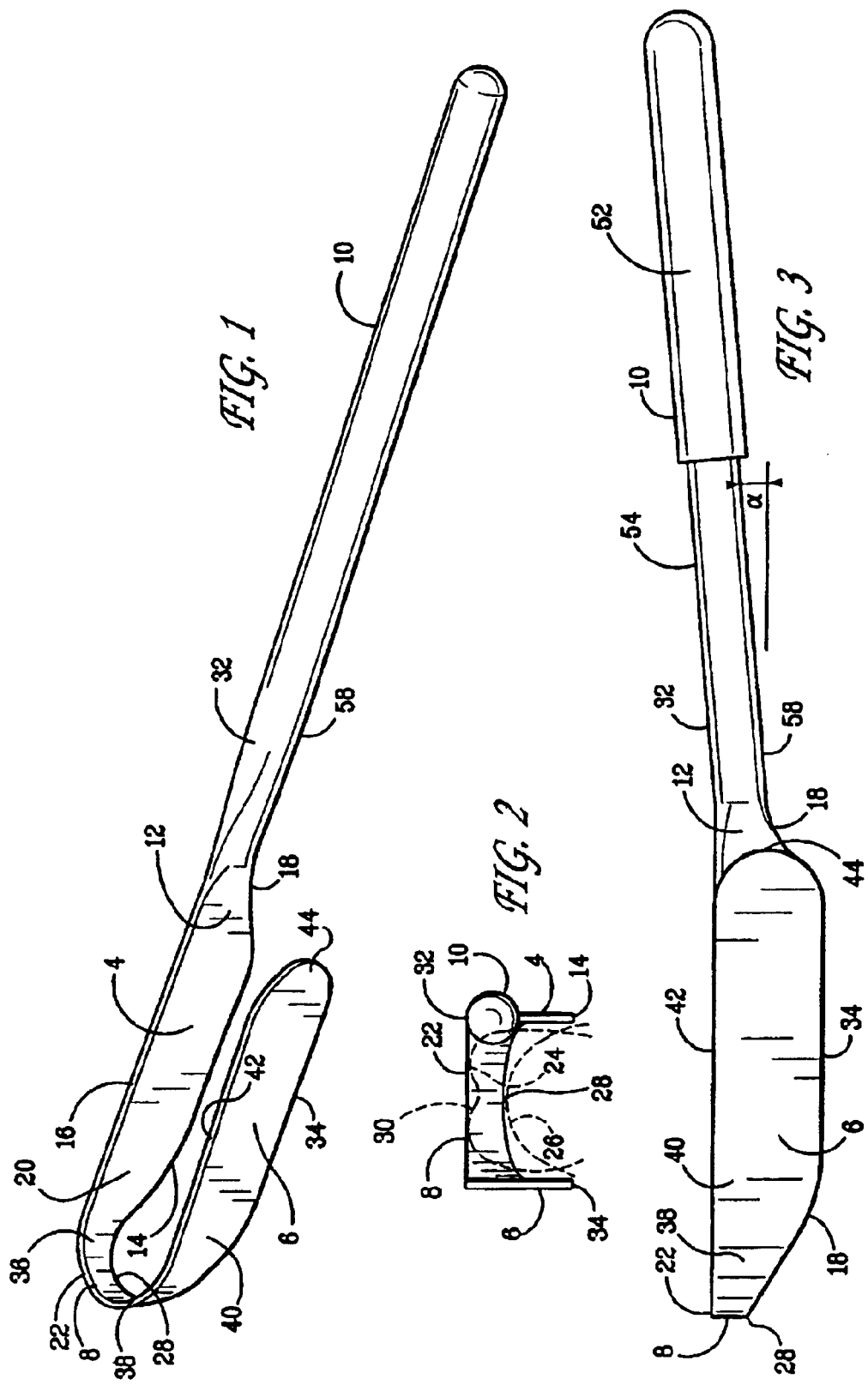

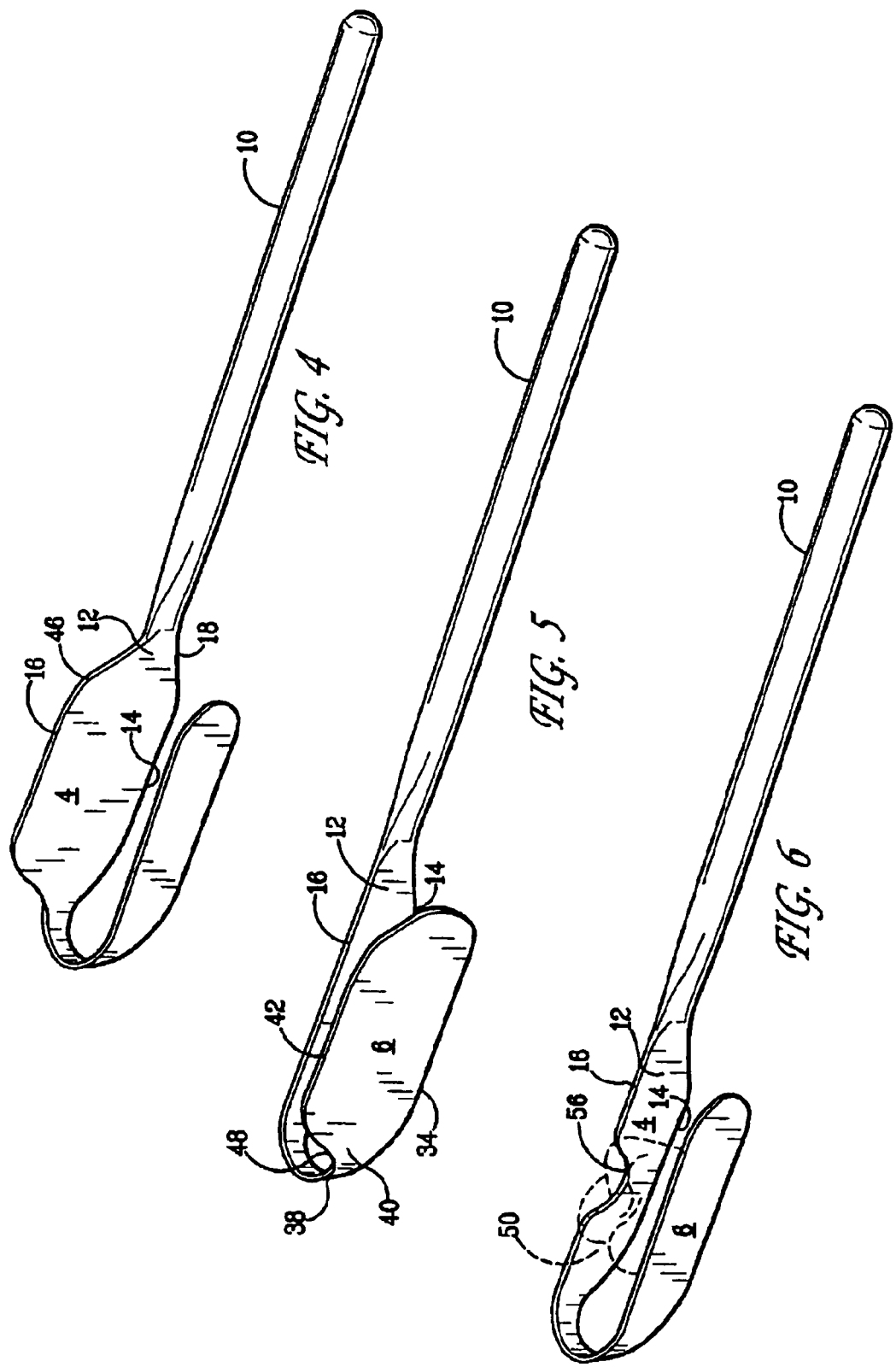

CHEEK, LIP AND TONGUE SHIELD

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure, as it appears in the Patent and Trademark Office patent files or records, but otherwise reserves all copyright and trade dress rights whatsoever.

FIELD OF THE INVENTION

This invention relates generally to dental instruments, and in particular, to a cheek, lip and tongue shield for use during intraoral procedures.

BACKGROUND OF THE INVENTION

During intraoral operative procedures, and in particular during dental operative procedures, it is vital to maintain both a clear visual field of the operative site and to prevent iatrogenic damage to the surrounding hard and soft tissue. This is most often accomplished by retracting and/or physically preventing the cheek and tongue from contacting or blocking both the operative site and instrumentation such as dental rotary handpieces (drills), scalers, curettes, scalpels, forceps and the like. Isolation of the check, lip and tongue is also required for many non-operative dental procedures, such as the taking of dental impressions.

The art is replete with devices designed to isolate the cheek, lip and/or tongue. For example, U.S. Pat. No. 730,184 to Witter is directed to a retractor in the form of a U shaped frame having a buccal side, a lingual side and a detachable handle. The sides are connected anteriorly by a hinged connection which transverses the dental arch. The hinged connection permits the contraction or expansion of the frame to facilitate the engagement or disengagement of the teeth and to regulate the width of the opening to accommodate differing patients. A thumb wheel controls the expansion and contraction of the frame. A tooth clamp optionally holds the retractor in place.

U.S. Pat. No. 1,474,497 to Stolper is directed to a Z-shaped in cross section retractor. Extending from a shank at one end at a substantially right angle is a tongue and lip shield, and extending from the other end at a substantially right angle in the opposite direction is a cheek shield. The shank also serves as a handle. The shields transverse the dental arch anteriorly.

U.S. Pat. No. 2,125,980 to Basil is directed to a retractor having a tongue depressing element, a cheek retracting element, and a mirror. The tongue depressing element is connected with the free end of a rod which serves as a handle, the cheek retracting element is positioned adjacent to the handle, and the mirror is located between the cheek retracting element and the tongue depressing element. The handle is held such that it does not interfere with the dental arch.

U.S. Pat. No. 2,831,480 to Milano is directed to a retractor having a handle connected to a U shaped retraction element. The U shaped element contains a cheek retractor connected by a bridge containing recesses in width to allow for extension over the dental arch. While the upper and lower edges of the bridge contain a recess, there is sufficient extent between the recesses to insure the patient maintains adequate vertical opening. A tongue engaging element is joined at the outer end of the bridge.

U.S. Pat. No. 4,112,934 to Rizk is directed to a device for protecting the teeth and alveolar ridge during placement of a laryngoscope having a handle connected to a protective member. The protective member straddles the alveolar ridge and teeth preventing contact with the laryngoscope.

U.S. Pat. No. 5,873,718 to Sullivan is directed to a retractor having a hollow tube configured with a middle protrusion for tongue retraction and outer wings to retain the cheek and lip retractors.

U.S. Pat. No. 5,890,899 to Sclafani is directed to a retractor and jaw prop having a prop stem, a maxillary support secured to the prop stem, a buccal member depending angularly from the bottom of the prop stem, and a lingual member extending from the bottom of the prop stem and away from the buccal member. The buccal and lingual members are disposed on opposite sides of the dental arch, with the connecting member transversing the dental arch anteriorly.

U.S. Pat. No. 6,213,772 to Costello is directed to a retractor having a buccal shield and a lingual shield connected by an elastic hinge. Both buccal shield and lingual shield are hollow with orifices in communication with the oral cavity, essentially ovoid in shape, and contain a divider. Where the retractor exits the mouth, provision is made for attachment of high volume and low volume suction. The elastic hinge is used to provide a lateral expansion force to both the buccal shield and lingual shield to aid in retraction of the cheek and tongue.

These and other conventional retractor designs used to isolate the lip, cheek and tongue generally apply a force directed outwardly to either "push" or "pull" the soft tissue away from the operative field. Those designs which permit individual retraction of a lip or a cheek, but do not permit simultaneous retraction of both the lip and the cheek allow the to droop into the operative field when the cheek is retracted. Conversely, those designs allow the cheek to droop into the operative field when the lip is retracted.

Positive forces applied to retract soft tissues such as the cheek, lip and tongue can cause post operative patient muscle fatigue and/or pain, particularly if the forces are applied for extended time or applied excessively. Additionally, active retraction, particularly in patients with strong or heavy facial musculature, can cause clinician hand and arm fatigue, especially when repeated on multiple patients throughout the day.

Accordingly, there remains a need for a device that will maintain a clear operative field and prevent iatrogenic soft tissue damage without causing either patient or clinician muscle fatigue and pain. The present invention fulfills this need, and further provides related advantages.

SUMMARY OF INVENTION

The present invention comprises a first shield, second shield, non-hinging transverse member separating the first and second shield, and a handle extending from the first shield. When placed intraorally, the first shield passively isolates the cheek and lip and the second shield passively isolates the tongue from the operative site.

The handle has a first and second end, the first end for gripping; the first shield has an anterior end, a posterior end, and an inferior border, the anterior end transitioning from the handle second end; the non-hinging transverse member has a first and second end, the first end transitioning from the first shield posterior end; and the second shield has an anterior end, a posterior end, and an inferior border, the posterior end transitioning from the transverse member second end. The transverse member inferior border does not extend as far inferiorly as the first and second shield inferior borders.

The present invention also comprises the method of using a non-hinging cheek, lip and tongue shield to isolate a tooth, teeth or portion of the alveolar ridge during dental treatment.

One advantage of the present invention is that the first and second shield create no outward pressure on soft tissue, thereby reducing the risk for patient post operative discomfort.

A second advantage of the present invention is that clinician fatigue is reduced.

Other features and advantages of the present invention will be apparent from the following more detailed description of the preferred embodiment, taken in conjunction with the accompanying drawings which illustrate, by way of example, the principles of the invention.

BRIEF DESCRIPTION OF DRAWINGS

FIG. 1 is a perspective view of the present invention;

FIG. 2 is an end view of the present invention;

FIG. 3 is a side view of the present invention with a handle and shaft;

FIG. 4 is a perspective view of a second embodiment of the present invention;

FIG. 5 is a perspective view of a third embodiment of the present invention; and FIG. 6 is a perspective view of the present invention with a shield access area.

DETAILED DESCRIPTION

The present invention as depicted in the figures discloses a cheek, lip and tongue shield for use in the mandibular left and maxillary right quadrants. It should be obvious to one skilled in the art that a mirror image design would be applicable for use in the mandibular right and maxillary left quadrants.

Referring to FIGS. 1 and 2, the primary components of the present invention comprise a first shield 4, second shield 6, non-hinging transverse member 8 separating the first and second shield 4, 6, and a handle 10. The component parts are preferably fabricated from a substantially rigid, preferably lightweight material, for example, metal such as die cast, extruded, or rolled aluminum; aluminum alloy; carbon, surgical, and stainless steel; molded plastic; layed up laminate plastic; and combinations thereof.

The component parts are preferably fabricated from a material that may be sterilized, for example, heat sterilized in, for example, an autoclave or dry heat oven. When surgical stainless steel or other metals are utilized, preferably they are highly polished to provide a reflective surface.

The present invention may be fabricated, for example by a casting or molding to create a device of unitary construction, or the handle may be fabricated separately and fastened, for example, by screwing, welding, spot welding or adhering to the remaining components, as described in detail below.

Handle 10 is preferably round or hexagonal in cross section, however, should be understood that handle 10 may be a cross section of any geometric shape that will permit effective gripping. Handle 10 transitions into anterior end 12 of first shield 4. First shield 4 is, for example, a buccal shield utilized as a barrier to isolate the cheek and lip (not shown) from iatrogenic trauma, and to prevent the cheek and lip from encroaching on the operative site.

Optionally, as shown in FIG. 3, handle 10 may include anterior grip 52 and shaft 54. Anterior grip 52 has a cross section of any shape that will permit effective gripping. Shaft 52 extends posteriorly from anterior grip 52 to transition into first shield anterior end 12.

First shield 4 is substantially planar (flat) in shape, oriented in a substantially vertical dimension. First shield 4 is dimensioned such that an inferior border 14 extends below the gingival margin (not shown) and a superior border 16 extends to the level of or above or below (FIG. 6) the occlusal table 30. First shield length is determined by the number of teeth desired to be isolated.

In a first, preferred embodiment, handle 10 transitions into first shield anterior end 12. Handle superior border 32 transitions into first shield superior border 16. Because first shield 4 has a greater vertical dimension than handle 10, first shield inferior border 14 smoothly transitions into handle inferior border 58 through, for example a slope radius 18 of effective inclination or curvature to prevent the creation of sharp corners which could irritate the lip or cheek.

Although optional, to facilitate practitioner comfort and minimize practitioner hand fatigue, handle 10 is angled at angle $α$. Angle $α$ is preferably between about $-85°$ and about $+85°$, more preferably between about $-45°$ and about $+45°$, and most preferably about $10°$.

Posterior end 20 of first shield 4 transitions into first end 36 of transverse member 8. First shield superior border 16 transitions into transverse member superior border 22. In order to cross the dental 24 or alveolar ridge 26, yet still maintain effective placement of first and second shield inferior borders 14, 34 below the gingival margin, transverse member inferior border 28 does not extend as far inferiorly as does first and second shield inferior borders 14, 34. First shield inferior border 14 transitions into transverse member inferior border 28 with, for example, slope or radius 18 of effective inclination or curvature to prevent the creation of sharp corners, thereby increasing patient comfort.

Transverse member 8 is non-hinged, substantially prohibiting flexure of first and second shields 4, 6. Transverse member 8 has a radius in the occlusal plane, thereby creating the U-shape which permits first and second shield 4, 6 to position on both sides of the dental arch.

Transverse member second end 38 transitions into second shield posterior end 40. Transverse member superior border 22 transitions into second shield superior border 42. Transverse member inferior border 28 transitions into second shield inferior border 34 with, for example, slope or radius 18 of effective inclination or curvature to prevent the creation of sharp corners, thereby increasing patient comfort. Second shield 6 is, for example, a lingual shield utilized as a barrier to isolate and protect the tongue (not shown) from iatrogenic trauma, and to prevent the tongue from encroaching on the operative site.

Second shield 6 is substantially planar (flat) in shape, oriented in a substantially vertical dimension. Second shield 6 is dimensioned such that second shield inferior border 34 extends below the gingival margin (not shown) and second shield superior border 42 extends to the level of or above or below (FIG. 6) occlusal table 30. Second shield anterior end 44 is rounded for patient comfort.

Optionally, second shield 6 is "cupped" throughout a substantial portion of its length on its lingual side, and/or flared lingually at anterior end 44 to help engage and passively isolate the tongue.

Referring to FIG. 4, in a second preferred embodiment, handle 10 transitions into first shield anterior end 12 at a predetermined location between first shield superior border 16 and first shield inferior border 14. Handle 10 transitions into first shield inferior border 14 through, for example, a first slope or radius 18 and into first shield superior border 16 through, for example, a second slope or radius 46, both of which are of an effective inclination or curvature to avoid the creation of sharp corners which could irritate the lip. In this embodiment, the vertical dimension of the first shield 4 may be extended to provide increased isolation to protect the cheek and lip (not shown) from iatrogenic trauma, and to prevent the cheek and lip from encroaching on the operative site. In all other respects, this embodiment is the same as the first embodiment described above.

Likewise, referring to FIG. 5, second shield 6 vertical dimension may be extended to provide increased isolation to protect the tongue (not shown) from iatrogenic trauma, and to further prevent the tongue from encroaching on the operative site. In this third preferred embodiment, transverse member second end 38 transitions into second shield posterior end 40 at a predetermined location between second shield inferior border 34 and second shield superior border 42 through, for example, a slope or radius 48 of an effective inclination or curvature to avoid the creation of sharp corners which could irritate the tongue. In all other respects, this embodiment is the same as the first embodiment described above.

It should also be appreciated the second and third embodiment described above may be combined to produce a fourth embodiment (not shown) having both a first and second shield 4, 6 of extended vertical dimension.

Referring to FIG. 6, first shield 4, second shield 6, or both may have at least one predetermined shield area removed to create an access opening, for example, a semi-circular shaped access opening 56 to provide operative access to, for example, a buccal or lingual surface of tooth 50. Semi-circular access opening 56 may be machined into first or second shield 4, 6 during the manufacturing process, or it may be created by the clinician using, for example, rotary instrumentation, for a custom positioned access opening 56. A shield manufactured of molded plastic particularly lends itself to an access opening custom created by the clinician.

In use, the clinician places the present invention over a preselected area of the dental arch to isolate the tooth or teeth is be treated. Additionally, the present invention may be utilized to hold a moisture barrier, for example, a cotton roll or "dri-angle" in place.

Although the present invention has been described with reference to exemplary embodiments, it is not limited thereto. Rather, the appended claims should be construed to include other variants and embodiments of the invention which may be made by those skilled in the art without departing from the true spirit and scope of the present invention.

What is claimed is:

1. A cheek, lip and tongue shield comprising:
    a handle having a first and second end, the first end for gripping;
    a substantially flat first shield having an anterior end, a posterior end, and an inferior border, the anterior end transitioning from the handle second end;
    a non-hinging transverse member having a first end, a second end, and an inferior border, the first end transitioning from the first shield posterior end; and
    a second shield having an anterior end, a posterior end, and an inferior border, the posterior end transitioning from the transverse member second end;
    wherein the transverse member inferior border does not extend as far inferiorly as the first and second shield inferior borders, the first shield passively isolates the cheek and lip from an operative site, the second shield passively isolates the tongue from the operative site at least one of a shield superior border selected from the group consisting of a first and second shield superior border is located below an occlusal table and the transverse member is positioned to cross an alveolar ridge.

2. A cheek, lip and tongue shield comprising:
    a handle having a first and second end, the first end for gripping;
    a first shield having an anterior end, a posterior end, a superior border and an inferior border, the anterior end transitioning from the handle second end;
    a non-hinging transverse member having a first end, a second end, and an inferior border, the first end transitioning from the first shield posterior end; and
    a second shield having an anterior end, a posterior end, a superior border and an inferior border, the posterior end transitioning from the transverse member second end;
    wherein at least one of the shield superior borders selected from the group consisting of the first and second shield superior border is located below an occlusal table, the transverse member inferior border does not extend as far inferiorly as the first and second shield inferior borders, the first shield passively isolates the cheek and lip from an operative site, and the second shield passively isolates the tongue from the operative site.

3. The cheek, lip and tongue shield of claim 2 wherein the component parts are fabricated from a material that may be sterilized.

4. The cheek, lip and tongue shield of claim 2 wherein the first and second shield are highly polished to provide a reflective surface.

5. The cheek, lip and tongue shield of claim 2 wherein the component parts are of a unitary construction.

6. The cheek, lip and tongue shield of claim 2 wherein the handle is fastened to the first shield anterior end.

7. The cheek, lip and tongue shield of claim 6 wherein the handle is fastened to the first shield anterior end by any one of the methods selected from the group consisting of screwing, welding, spot welding or adhering.

8. The cheek, lip and tongue shield of claim 2 wherein the handle has a cross section of any geometric shape that will permit effective gripping.

9. The cheek, lip and tongue shield of claim 2 wherein the handle further comprises an anterior grip and a shaft, the shaft transitioning into the first shield anterior end.

10. The cheek, lip and tongue shield of claim 2 wherein the first and second shield are substantially planar in shape and oriented in a substantially vertical dimension.

11. The cheek, lip and tongue shield of claim 2 wherein the second shield further includes at least one selected from the group consisting of an anterior flare and cupping throughout a substantial portion of its length on its lingual side.

12. The cheek, lip and tongue shield of claim 2 wherein an inferior border of the first and second shields extends below a gingival margin and the superior border of the first and second shields extends to at least the level of an occlusal table.

13. The cheek, lip and tongue shield of claim 2 wherein the length of the first and second shields is an effective length to cover a predetermined number of teeth.

14. The cheek, lip and tongue shield of claim 2 wherein a handle superior border transitions into the first shield superior border and a handle inferior border transitions into the first shield inferior border through the use of a transition selected from the group consisting of a slope and a radius of effective inclination and curvature to prevent the creation of sharp corners.

15. The cheek, lip and tongue shield of claim 2 wherein the handle is set at an angle to the first shield.

16. The cheek, lip and tongue shield of claim 15 wherein the angle is between about −85° and about +85°.

17. The cheek, lip and tongue shield of claim 15 wherein the angle is between about −45° and about −45°.

18. The cheek, lip and tongue shield of claim 15 wherein the angle is about 10°.

19. The cheek, lip and tongue shield of claim 2 wherein the transverse inferior border transitions into the first and second shield inferior border through the use of a transition selected from the group consisting of a slope and a radius of effective inclination and curvature to prevent the creation of sharp corners.

20. The cheek, lip and tongue shield of claim 2 wherein the handle transitions into the first shield anterior end at a predetermined location between the first shield superior border and the first shield inferior border, the handle superior and inferior borders transitioning through the use of a transition selected from the group consisting of a slope and a radius of effective inclination and curvature to prevent the creation of sharp corners.

21. The cheek, lip and tongue shield of claim 2 wherein the transverse member second end transitions into the second shield posterior end at a predetermined location between the second shield superior border and the second shield inferior border, the transverse member superior and inferior borders transitioning through the use of a transition selected from the group consisting of a slope and a radius of effective inclination and curvature to prevent the creation of sharp corners.

22. The cheek, lip and tongue shield of claim 2 wherein
the handle transitions into the first shield anterior end at a predetermined location between the first shield superior border and the first shield inferior border, the handle superior and inferior borders transitioning through the use of a transition selected from the group consisting of a slope and a radius of effective inclination and curvature to prevent the creation of sharp corners; and
the transverse member second end transitions into the second shield posterior end at a predetermined location between the second shield superior border and the second shield inferior border, the transverse member superior and inferior borders transitioning through the use of a transition selected from the group consisting of a slope and a radius of effective inclination and curvature to prevent the creation of sharp corners.

23. The cheek, lip and tongue shield of claim 2 wherein at least one selected from the group consisting of the first shield and the second shield further includes an access opening.

24. The cheek, lip and tongue shield of claim 2 wherein a second shield anterior end is rounded.

25. A method for passively isolating a dental arch comprising the steps of
a) selecting an area of the dental arch to be isolated; and
b) inserting a cheek, lip and tongue shield over the selected area of the dental arch;
wherein the cheek, lip and tongue shield comprises
a handle having a first and second end, the first end for gripping;
first shield having an anterior end, a posterior end, a superior border and a inferior border, the anterior end transitioning from the handle second end;
a non-hinging transverse member having a first end, a second end, and an inferior border, the first end transitioning from the first shield posterior end; and
a second shield having an anterior end, a posterior end, a superior border and an inferior border, the posterior end transitioning from the transverse member second end;
wherein at least one of the shield superior borders selected from the group consisting of the first and second shield superior border is located below an occlusal table, the transverse member inferior border does not extend as far inferiorly as the first and second shield inferior borders, the first shield passively isolates the cheek and lip, from an operative site, and the second shield passively isolates the tongue from the operative site.

26. The method of claim 25 further including the step of securing a moisture barrier with the cheek, lip and tongue shield.

27. The method of claim 25 wherein the first shield is substantially flat.

* * * * *